US012758449B2

(12) United States Patent
Dzioba

(10) Patent No.: US 12,758,449 B2
(45) Date of Patent: Oct. 13, 2026

(54) SUPPORT SURFACE OVERLAY WITH ACOUSTIC PATIENT DETECTION

(71) Applicant: Raye's, Inc., Eden Prairie, MN (US)

(72) Inventor: David A. Dzioba, Freeland, MI (US)

( * ) Notice: Subject to any disclaimer, the term of this patent is extended or adjusted under 35 U.S.C. 154(b) by 223 days.

(21) Appl. No.: 18/647,697

(22) Filed: Apr. 26, 2024

(65) Prior Publication Data

US 2024/0358569 A1 Oct. 31, 2024

Related U.S. Application Data

(60) Provisional application No. 63/462,480, filed on Apr. 27, 2023.

(51) Int. Cl.

*A61G 7/057* (2006.01)
*A47C 27/08* (2006.01)
*A61B 5/00* (2006.01)

(52) U.S. Cl.

CPC ........ *A61G 7/05776* (2013.01); *A47C 27/082* (2013.01); *A47C 27/083* (2013.01); *A61B 5/447* (2013.01); *A61B 5/6892* (2013.01); *A61B 2562/0204* (2013.01); *A61B 2562/0219* (2013.01)

(58) Field of Classification Search

CPC ..... A47C 27/08; A47C 27/081; A47C 27/082; A47C 27/083; A47C 27/084; A47C 27/085; A47C 27/086; A47C 27/087; A47C 27/088; A47C 27/10; A61B 5/447; A61B 5/6892; A61B 2562/0204; A61B 2562/0219; A61G 7/05776

See application file for complete search history.

(56) References Cited

U.S. PATENT DOCUMENTS 5,325,551 A * 7/1994 Tappel ................. A47C 27/082 5/709
6,327,727 B1 12/2001 Bocharnikov
10,314,407 B1 * 6/2019 Main .................... A61B 5/1036
11,253,079 B1 * 2/2022 Kahn ................... A47C 27/083
2004/0136550 A1 * 7/2004 Park ..................... A47C 21/006 381/301
2008/0189865 A1 8/2008 Bhai
2009/0100604 A1 4/2009 Caminade et al.
2012/0079662 A1 * 4/2012 Dzioba ................... A61F 2/602 5/713

(Continued)

*Primary Examiner* — George Sun

(74) *Attorney, Agent, or Firm* — Spencer Fane LLP

(57) ABSTRACT

A support surface overlay system includes a support surface overlay and a control system. The support surface overlay includes at least one selectively inflatable compartment. The control system includes a pneumatic controller configured to inflate and deflate the at least one selectively inflatable compartment. The control system also includes a memory, a sensor, and a processor. The memory is programmed with a predetermined data indicative of an operating parameter of the system vs. time with the support surface overlay in an unloaded state. The sensor is configured to detect and provide signals indicative of the operating parameter of the system vs. time during inflation and/or deflation of the at least one selectively inflatable compartment. The processor is configured to compare the predetermined data to the data provided by the sensor and to determine whether or not a load is present on the support surface overlay based on the comparison.

7 Claims, 3 Drawing Sheets

(56) References Cited

U.S. PATENT DOCUMENTS

| | | | | |
|---|---|---|---|---|
| 2012/0137440 | A1* | 6/2012 | Richards | A61G 7/16<br>5/713 |
| 2018/0280219 | A1* | 10/2018 | Garrett | A61G 7/001 |
| 2019/0106093 | A1* | 4/2019 | Lemaitre | B60T 8/171 |
| 2019/0200777 | A1* | 7/2019 | Demirli | A61B 5/7267 |
| 2019/0350747 | A1* | 11/2019 | Hariri | A61F 5/56 |
| 2021/0085091 | A1* | 3/2021 | Brandt | A47C 27/082 |
| 2021/0295661 | A1* | 9/2021 | Tadele | A61B 5/6892 |
| 2021/0338506 | A1 | 11/2021 | Dzioba et al. | |
| 2022/0125217 | A1* | 4/2022 | Connor | A47C 27/061 |
| 2024/0188726 | A1* | 6/2024 | Karschnik | A47C 27/084 |

* cited by examiner

SUPPORT SURFACE OVERLAY WITH ACOUSTIC PATIENT DETECTION

CROSS-REFERENCE TO RELATED APPLICATIONS

The present U.S. non-provisional patent application is related to and claims priority benefit to an earlier-filed provisional patent application titled SUPPORT SURFACE OVERLAY WITH ACOUSTIC PATIENT DETECTION, Ser. No. 63/462,480 filed Apr. 27, 2023. The identified earlier-filed application is hereby incorporated by reference into the present application as though fully set forth herein.

TECHNICAL FIELD

The disclosed subject matter relates generally to a support surface overlay, and more particularly, to a support surface overlay system having a patient detection system configured to selectively inflate and deflate a bladder and to detect the presence of a load on the bladder.

BACKGROUND

Support surface overlays for mitigation and prevention of decubitus ulcers are known in the art. Such support surface overlays may include first and second selectively and alternatingly inflatable compartments configured to reduce contact pressure against a patient's skin. Some such support surface overlays have a limited service life, which service life may be a function of the number of hours the overlay is in use and supporting a patient. It would be desirable to provide the ability to detect and monitor actual patient use of such support surface overlays.

SUMMARY

These and other features of the disclosed subject matter are described in greater detail below in the section titled DETAILED DESCRIPTION.

In some aspects, the subject matter described herein relates to a support surface overlay system including: a bladder having a first selectively inflatable compartment and a first fluid conduit in fluid communication with the first selectively inflatable compartment; and a control system configured to selectively inflate and deflate the bladder and to detect a presence of a load on the bladder, the control system including: a controller having a pump configured to selectively inflate and deflate the first selectively inflatable compartment and a pump outlet conduit in fluid communication with the pump; a memory configured to store predetermined data indicative of a first operating parameter related to inflation and deflation of the first selectively inflatable compartment with the bladder in an unloaded state as a function of time; a first sensor configured to detect and provide data signals indicative of the first operating parameter related to inflation and deflation of the first selectively inflatable compartment as a function of time; and a processor configured to receive the data signals from the first sensor, compare the data signals received from the first sensor to the predetermined data stored in the memory according to a predetermined criteria, and determine whether or not a load is present on the bladder based on the comparison.

In some aspects, the subject matter described herein relates to a support surface overlay system, wherein the first operating parameter includes sound in, on, or near one of the first fluid conduit and the pump outlet conduit as a function of time; wherein the predetermined data stored in the memory is indicative of the sound in, on, or near the one of the first fluid conduit and the pump outlet conduit as a function of time; and wherein the first sensor includes a first acoustic sensor configured to detect the sound in, on, or near the one of the first fluid conduit and the pump outlet conduit as a function of time.

In some aspects, the subject matter described herein relates to a support surface overlay system, wherein the predetermined data stored in the memory includes at least one of a duration, a timing, or a pitch characteristic; and wherein the predetermined criteria includes a predetermined difference between at least one of the duration, the timing, or the pitch characteristic of the predetermined data stored in the memory and a corresponding one of a duration, a timing, or a pitch characteristic of the sound detected by the first sensor.

In some aspects, the subject matter described herein relates to a support surface overlay system, wherein the support surface overlay system further includes an exhaust conduit in fluid communication with the first selectively inflatable compartment and configured to discharge fluid from the first selectively inflatable compartment; wherein the first operating parameter includes sound in, on, or near the exhaust conduit as a function of time; wherein the predetermined data stored in the memory is indicative of the sound in, on, or near the exhaust conduit as a function of time; and wherein the first sensor includes a first acoustic sensor configured to detect the sound in, on, or near the exhaust conduit as a function of time.

In some aspects, the subject matter described herein relates to a support surface overlay system, wherein the predetermined data stored in the memory includes at least one of a duration, a timing, or a pitch characteristic; and wherein the predetermined criteria includes a predetermined difference between at least one of the duration, the timing, or the pitch characteristic of the predetermined data stored in the memory and a corresponding one of a duration, a timing, or a pitch characteristic of the sound detected by at least one of the first sensor and a second sensor.

In some aspects, the subject matter described herein relates to a support surface overlay system, wherein the support surface overlay system further includes an exhaust conduit in fluid communication with the first selectively inflatable compartment and configured to discharge fluid from the first selectively inflatable compartment; wherein the first operating parameter includes sound in, on, or near the exhaust conduit as a function of time; wherein the predetermined data stored in the memory is indicative of the sound in, on, or near the exhaust conduit as a function of time, and wherein the first sensor includes a first acoustic sensor configured to detect the sound in, on, or near the exhaust conduit as a function of time.

In some aspects, the subject matter described herein relates to a support surface overlay system, wherein the predetermined data stored in the memory includes at least one of a duration, a timing, or a pitch characteristic, and wherein the predetermined criteria includes a predetermined difference between at least one of the duration, the timing, or the pitch characteristic of the predetermined data stored in the memory and a corresponding one of a duration, a timing, or a pitch characteristic of the sound detected by the first acoustic sensor.

In some aspects, the subject matter described herein relates to a support surface overlay system, wherein the load may include a patient.

In some aspects, the subject matter described herein relates to a support surface overlay system, wherein the bladder further including: a second selectively inflatable compartment and a second fluid conduit in fluid communication with the second selectively inflatable compartment, wherein the pump is configured to selectively inflate and deflate the second selectively inflatable compartment; a second sensor configured to detect and provide data signals indicative of a second operating parameter related to inflation and deflation the second selectively inflatable compartment as function of time, wherein the processor is further configured to receive data signals form the second sensor, compare the data signals received from the second sensor to the predetermined data stored in the memory according to the predetermined criteria, and determine whether or not a load is present on the bladder based on the comparison.

In some aspects, the subject matter described herein relates to a support surface overlay system, wherein the first sensor includes one of a microphone and an accelerometer.

BRIEF DESCRIPTION OF THE FIGURES

The disclosed subject matter is described herein with reference to the following drawing figures, with greater emphasis being placed on clarity rather than scale.

DETAILED DESCRIPTION

Figure 1:
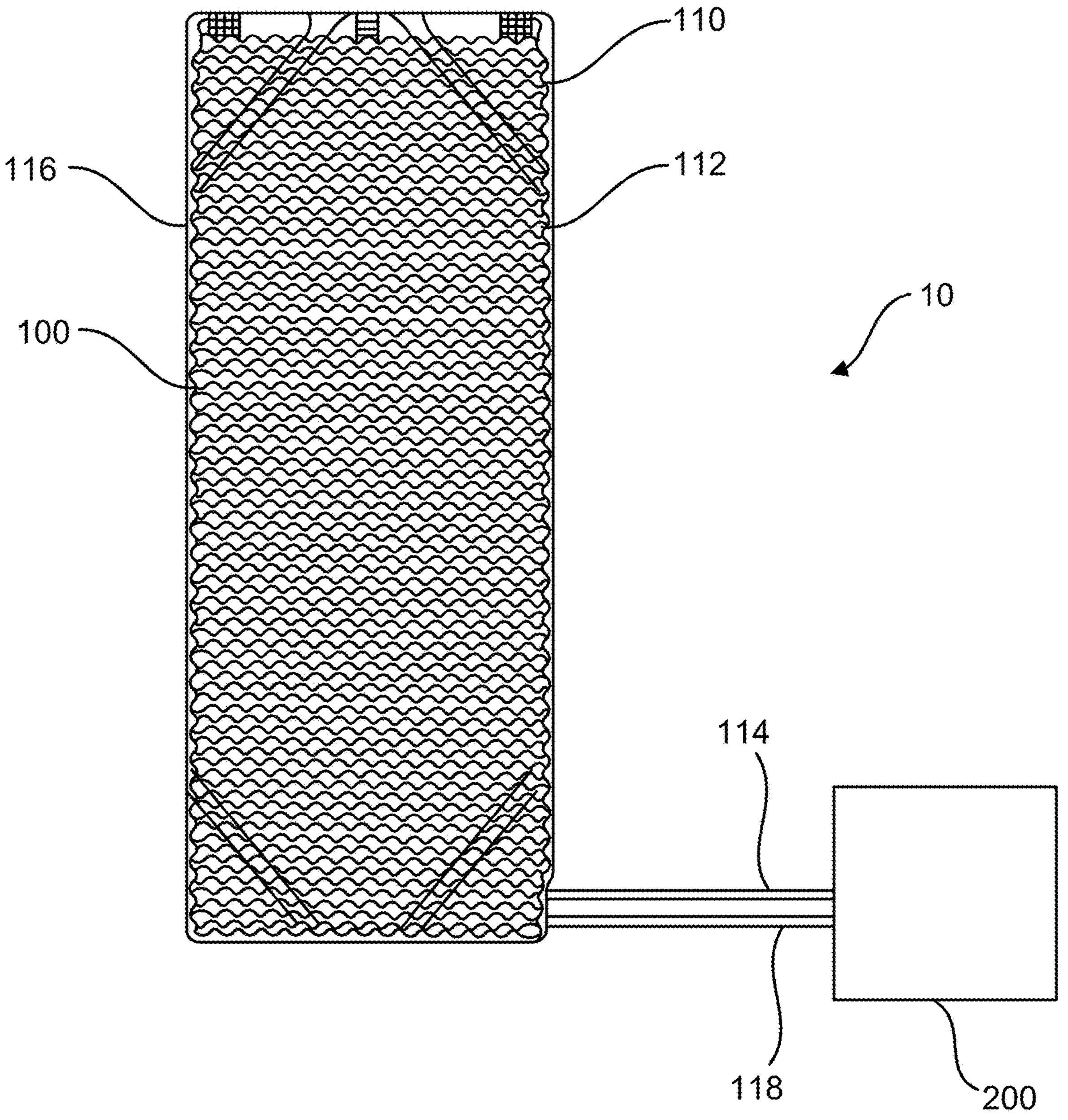
FIG. 1 is a illustrative support surface overlay with acoustic patient detection system according to the present disclosure.

As required, detailed aspects of the disclosed subject matter are disclosed herein; however, it is to be understood that the disclosed aspects are merely exemplary of the disclosed subject matter, which may be embodied in various forms. Therefore, specific structural and functional details disclosed herein are not to be interpreted as limiting, but merely as a basis for the claims and as a representative basis for teaching one skilled in the art how to variously employ the disclosed technology in virtually any appropriately detailed structure.

Although the disclosed subject matter has been disclosed with reference to various particular embodiments, it is understood that equivalents may be employed and substitutions made herein without departing from the scope of the disclosed subject matter as recited in the claims.

The disclosed subject matter will now be described with reference to the drawing figures, in which like reference numerals refer to like parts throughout. For purposes of clarity in illustrating the characteristics of the present disclosed subject matter, proportional relationships of the elements have not been maintained in the figures. In some cases, the sizes of certain small components have been exaggerated for illustration.

FIG. 1 illustrates an exemplary embodiment of a support surface overlay with patient detection system 10 according to the present disclosure. The system 10 includes a support surface overlay 100 and a control system 200. As will become apparent from the discussion below, portions of the control system 200 may be integrated into the support surface overlay 100.

Referring to FIG. 1, a support surface overlay 100 includes a bladder 110. The bladder 110 includes at least a first selectively inflatable compartment 112 and a first fluid conduit 114 in fluid communication with an interior region Z1 of the first selectively inflatable compartment 112. As shown, the bladder 110 also includes a second selectively inflatable compartment 116 and a second fluid conduit 118 in fluid communication with an interior region Z2 of the second selectively inflatable compartment 116. The second selectively inflatable compartment 116 is optional. As such, the second selectively inflatable compartment 116 and components related thereto as further described herein may be omitted in embodiments. In embodiments, the bladder 110 may further include additional selectively inflatable compartments and corresponding fluid conduits in fluid communication with interior regions thereof.

The control system 200 includes a pneumatic controller 202 including a pump 204 and an arrangement of valves, for example, a first three-way valve 206 and a second three-way valve 208, each configured to selectively inflate and deflate the first selectively inflatable compartment 112 and the second selectively inflatable compartment 116 by selectively admitting air or another fluid into, and relieving the air or another fluid from, the interior regions Z1, Z2 of the first selectively inflatable compartment 112 and the second selectively inflatable compartment 116. A processor 210 is coupled to the pump 204, the first three-way valve 206, and the second three-way valve 208 and is configured to control the operation thereof to effect inflation and deflation of the first selectively inflatable compartment 112 and the second selectively inflatable compartment 116, as would be recognized by one skilled in the art.

For example, the pneumatic controller 202 may be configured to inflate the first selectively inflatable compartment 112 and deflate the second selectively inflatable compartment 116 by aligning the first three-way valve 206 to allow fluid communication between the output of the pump 204 and the interior region Z1 of the first selectively inflatable compartment 112, aligning the second three-way valve 208 to allow fluid communication between the interior region Z2 of the second selectively inflatable compartment 116 and an exhaust conduit 219, and operating the pump 204 to inflate the first selectively inflatable compartment 112. In this alignment, the second selectively inflatable compartment 116 may be deflated by venting or discharging air or other fluid therein to an environment surrounding the support surface overlay 100 through the exhaust conduit 219. With the first selectively inflatable compartment 112 in the inflated state, the pneumatic controller 202 may be configured to hold the first selectively inflatable compartment 112 in the inflated state (that is, in a hold state) by aligning the first three-way valve 206 to isolate the interior region Z1 of the first selectively inflatable compartment 112 from the pump 204 and the exhaust conduit 219. In this hold state, the pump 204 may be turned off or cycled on and off as might be needed to maintain a desired pressure in the first selectively inflatable compartment 112.

Similarly, the pneumatic controller 202 may be configured to inflate the second selectively inflatable compartment 116 and deflate the first selectively inflatable compartment 112 by aligning the second three-way valve 208 to allow fluid communication between the output of the pump 204 and the interior region Z2 of the second selectively inflatable compartment 116, aligning the first three-way valve 206 to allow fluid communication between the interior region Z1 of the first selectively inflatable compartment 112 and the exhaust conduit 219, and operating the pump 204 to inflate the second selectively inflatable compartment 116. In this alignment, the first selectively inflatable compartment 112 may be deflated by venting or discharging air or other fluid therein to an environment surrounding the support surface overlay 100 through the exhaust conduit 219. With the second selectively inflatable compartment 116 in the inflated state, the pneumatic controller 202 may be configured to hold the second selectively inflatable compartment 116 in the inflated state by aligning the second three-way valve 208 to isolate the interior region Z2 of the second selectively inflatable compartment 116 from the pump 204 and the exhaust line. In this hold state, the pump 204 may be turned off or cycled on and off as might be needed to maintain a desired pressure in the second selectively inflatable compartment 116.

The control system 200 includes a first sensor configured to detect and provide an output indicative of a first operating parameter of the system 10. The control system 200 may also include a second sensor configured to detect and provide an output indicative of a second operating parameter of the system 10. In embodiments, the control system 200 may include additional sensors configured to detect and provide outputs indicative of additional operating parameters of the system 10. In embodiments, the sensors may be, for example and without limitation, acoustic sensors, for example, acoustic transducers or microphones. Similarly, the operating parameters may be, for example and without limitation, sound or noise in one or more portions of the system 10 detectable by the acoustic sensors.

For example, in the illustrated embodiment, the control system 200 includes a first acoustic sensor 214 physically associated with the first fluid conduit 114 in a manner that enables the first acoustic sensor 214 to detect and provide signals indicative of noise or other sound in or around the first fluid conduit 114. For example, the first acoustic sensor 214 may be disposed within the first fluid conduit 114, attached to an exterior surface of the first fluid conduit 114, or separated from the first fluid conduit 114 but nevertheless able to detect noise or other sound in or around the first fluid conduit 114. In embodiments, the first acoustic sensor 214 and its physical association with the first fluid conduit 114 may be shrouded by an anechoic or sound-deadening material to shield the first acoustic sensor 214 from ambient noise or other sound in an environment surrounding the first acoustic sensor 214 and its physical association with the first fluid conduit 114. The first acoustic sensor 214 is electrically coupled to the processor 210 so that the processor 210 may receive the signals provided by the first acoustic sensor 214.

The control system 200 of the illustrated embodiment also includes a second acoustic sensor 218 physically associated with the second fluid conduit 118 in a manner that enables the second acoustic sensor 218 to detect and provide signals indicative of noise or other sound in or around the second fluid conduit 118. For example, the second acoustic sensor 218 may be disposed within the second fluid conduit 118, attached to an exterior surface of the second fluid conduit 118, or separated from the second fluid conduit 118 but nevertheless able to detect noise or other sound or vibration in or around the second fluid conduit 118. In embodiments, the second acoustic sensor 218 and its physical association with the second fluid conduit 118 may be shrouded by an anechoic or sound-deadening material to shield the second acoustic sensor 218 from ambient noise or other sound in an environment surrounding the second acoustic sensor 218 and its physical association with the second fluid conduit 118. The second acoustic sensor 218 is electrically coupled to the processor 210 so that the processor 210 may receive the signals provided by the second acoustic sensor 218.

As shown, the control system 200 further includes a third acoustic sensor 220 physically associated with a pump outlet conduit 205 in a manner that enables the third acoustic sensor 220 to detect and provide signals indicative of noise or other sound in or around the pump outlet conduit 205. For example, the third acoustic sensor 220 may be disposed within the pump outlet conduit 205, attached to an exterior surface of the pump outlet conduit 205, or separated from the pump outlet conduit 205 but nevertheless able to detect noise or other sound in or around the pump outlet conduit 205. In embodiments, the third acoustic sensor 220 and its physical association with the pump outlet conduit 205 may be shrouded by an anechoic or sound-deadening material to shield the third acoustic sensor 220 from ambient noise or other sound in an environment surrounding the third acoustic sensor 220 and its physical association with the pump outlet conduit 205. The third acoustic sensor 220 is electrically coupled to the processor 210 so that the processor 210 may receive the signals provided by the third acoustic sensor 220.

As shown, the control system 200 still further includes a fourth acoustic sensor 222 physically associated with an exhaust conduit 219 in a manner that enables the fourth acoustic sensor 222 to detect and provide signals indicative of noise or other sound in or around the exhaust conduit 219. For example, the fourth acoustic sensor 222 may be disposed within the exhaust conduit 219, attached to an exterior surface of the exhaust conduit 219, or separated from the exhaust conduit 219 but nevertheless able to detect noise or other sound in or around the exhaust conduit 219. In embodiments, the fourth acoustic sensor 222 and its physical association with the exhaust conduit 219 may be shrouded by an anechoic or sound-deadening material to shield the fourth acoustic sensor 222 from ambient noise or other sound in an environment surrounding the fourth acoustic sensor 222 and its physical association with the exhaust conduit 219. The fourth acoustic sensor 222 is electrically coupled to the processor 210 so that the processor 210 may receive the signals provided by the fourth acoustic sensor 222.

The first acoustic sensor 214, the second acoustic sensor 218, third acoustic sensor 220, and the fourth acoustic sensor 222 may be, but need not be, microphones.

Figure 2:
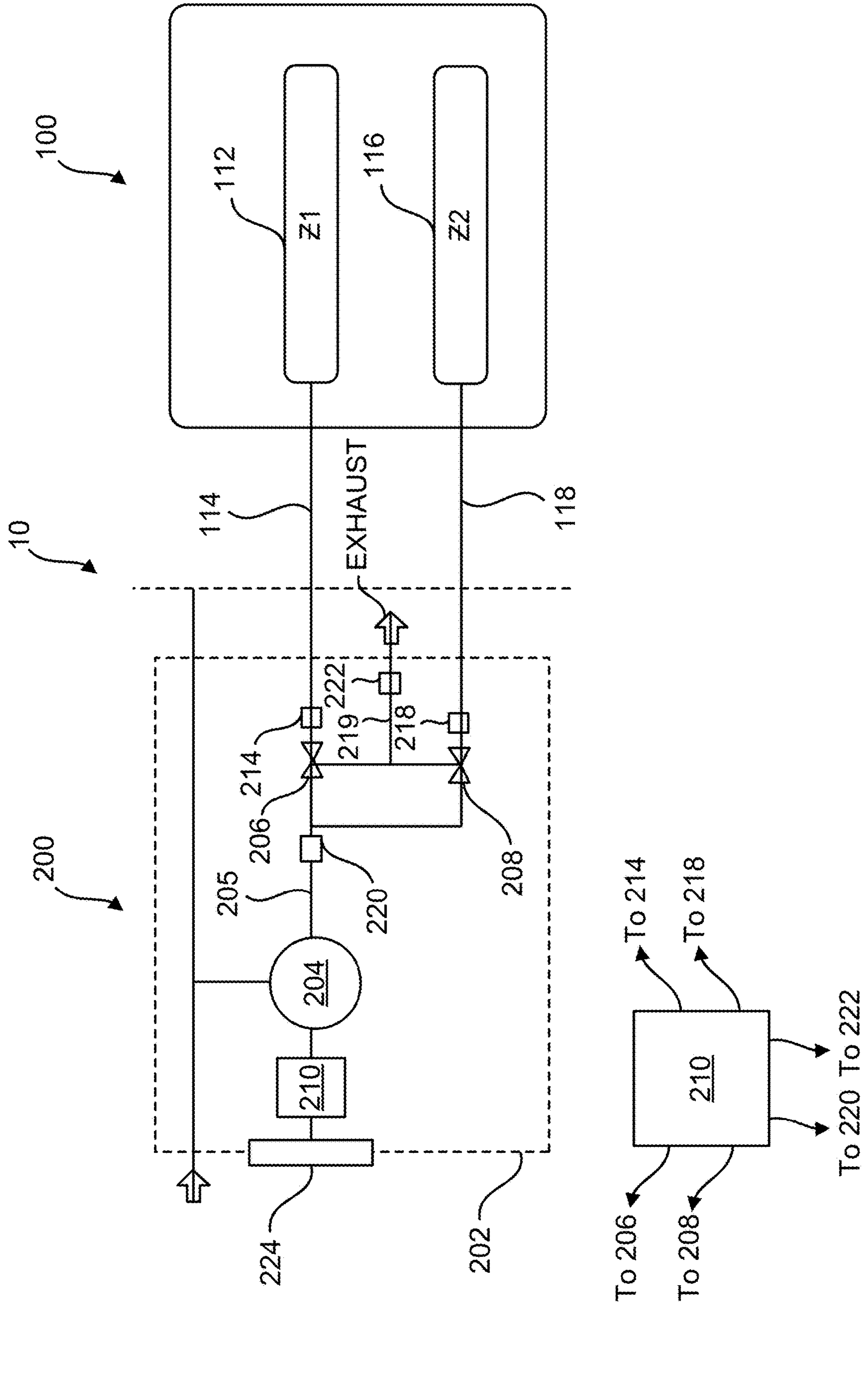
FIG. 2 is a schematic view of the system of FIG. 1.

Although embodiments of the system 10 may include all of the foregoing acoustic sensors, as shown in FIG. 2 and described above, only one of the foregoing acoustic sensors is necessary, and any and all other ones of the foregoing acoustic sensors may be omitted in other embodiments.

The control system 200 includes a memory 224 accessible by the processor 210. The memory 224 may be programmed with predetermined data indicative of one or more operating parameters of the system 10 without a load (for example, a patient or other mass) present on the support surface overlay 100. Such predetermined data may be real or theoretical.

That is, the predetermined data may be, for example, calculated based on known information regarding the construction of the support surface overlay 100 and the control system 200, or it may be determined empirically through operation of the system 10 with the support surface overlay 100 in an unloaded state.

Figure 3:
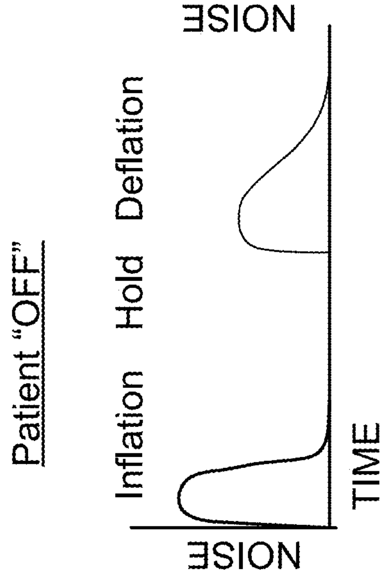
FIG. 3 is a plot of acoustic signal vs. time during an inflation phase, a hold phase, and a deflation phase of an inflatable compartment of the support surface overlay of the system of FIG. 1 in an unloaded state.

For example, in embodiments including the first acoustic sensor 214, the memory 224 may be programmed with predetermined data indicative of one or more predetermined profiles of noise or other sound in, on or near the first fluid conduit 114 as a function of time as the pneumatic controller 202 operates to selectively inflate and/or deflate the first selectively inflatable compartment 112 with no load on the support surface overlay 100. An illustrative graph showing such a profile of noise or other sound vs. time is shown in FIG. 3.

Similarly, in embodiments including the second acoustic sensor 218, the memory 224 may be programmed with predetermined data indicative of one or more predetermined profiles of noise or other sound in, on or near the second fluid conduit 118 as a function of time as the pneumatic controller 202 operates to selectively inflate and/or deflate the second selectively inflatable compartment 116 with no load on the support surface overlay 100.

Also, in embodiments including the third acoustic sensor 220, the memory 224 may be programmed with predetermined data indicative of one or more predetermined profiles of noise or other sound in, on or near the pump outlet conduit 205 as a function of time as the pneumatic controller 202 operates to selectively inflate and/or deflate the first selectively inflatable compartment 112 and/or the second selectively inflatable compartment 116 (based on the alignment of the first three-way valve 206 and the second three-way valve 208) with no load on the support surface overlay 100.

Further, in embodiments including the fourth acoustic sensor 222, the memory 224 may be programmed with predetermined data indicative of one or more predetermined profiles of noise or other sound in, on or near the exhaust conduit 219 as a function of time as the pneumatic controller 202 operates to selectively deflate the first selectively inflatable compartment 112 and/or the second selectively inflatable compartment 116 (based on the alignment of the first three-way valve 206 and the second three-way valve 208) with no load on the support surface overlay 100.

One skilled in the art would understand that the profiles of noise or other sound as a function of time detected by the foregoing acoustic sensors with a load present on the support surface overlay 100 would be different from the profiles of noise or other sound as a function of time with no load present on the support surface overlay 100. Such differences can be measured and evaluated to determine the presence of a user or other load on the support surface overlay 100, as discussed further below.

Figure 4:
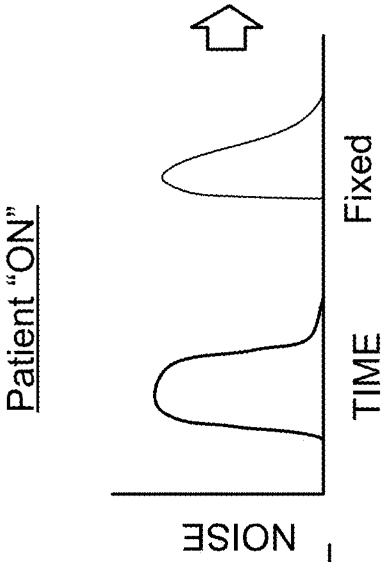
FIG. 4 is a plot of acoustic signal vs. time during an inflation phase, a hold phase, and a deflation phase of an inflatable compartment of the support surface overlay of the system of FIG. 1 in a loaded state.

For example, the pitch, timing, duration, or other characteristic of noise or other sound of noise or other sound at or around the acoustic sensors as the pneumatic controller 202 inflates and/or deflates the first selectively inflatable compartment 112 and/or the second selectively inflatable compartment 116 may differ depending on whether or not a user, patient, or other load is present on the support surface overlay 100. This phenomenon is illustrated in the graphs shown in FIGS. 3 and 4, with FIG. 3 being a graph of noise vs. time at or around one of the foregoing acoustic sensors as the first selectively inflatable compartment 112 and/or the second selectively inflatable compartment 116 are inflated and/or deflated with the support surface overlay 100 unloaded and FIG. 4 being a graph of noise vs. time at or around one of the foregoing acoustic sensors as the first selectively inflatable compartment 112 and/or the second selectively inflatable compartment 116 are inflated and/or deflated with the support surface overlay 100 having a load thereon.

Figure 5:
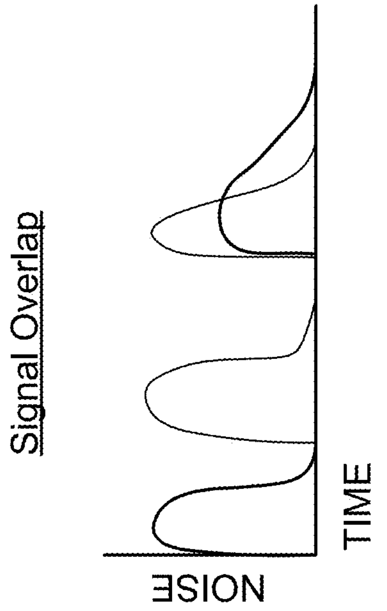
FIG. 5 is a plot of acoustic signal vs. time during an inflation phase, a hold phase, and a deflation phase of an inflatable compartment of the support surface overlay of the system of FIG. 1 in a loaded state superimposed on a plot of acoustic signal vs. time during an inflation phase, a hold phase, and a deflation phase of an inflatable compartment of the support surface overlay of the system of FIG. 1 in an unloaded state.

The processor 210 may be configured to compare the predetermined noise or other sound data for the support surface overlay 100 in an unload state stored in the memory 224, for example, as shown in FIG. 3, with the noise or other sound vs. time data provided by the first acoustic sensor 214 and/or the second acoustic sensor 218 as the first selectively inflatable compartment 112 and/or the second selectively inflatable compartment 116 of the support surface overlay 100 are inflated and/or deflated. The processor 210 is configured to determine a user, patient, or other load to be present on the support surface overlay 100 when the noise or other sound vs. time data provided by the first acoustic sensor 214 and/or the second acoustic sensor 218 differs from a predetermined criteria such as the noise or other sound vs. time data stored in the memory 224 in a predetermined way, for example, by more than a predetermined duration, timing, pitch or otherwise by a predetermined difference in the shape of a plot of noise or other sound vs. time. FIG. 5 illustrates an example of such differences that may be sufficient for the processor 210 to determine a user or other load present on the support surface overlay.

In embodiments, other operating parameters could be sensed and compared to corresponding data stored in the memory 224 in a similar manner. For example, pump vibration could be sensed by one or more accelerometers and compared to predetermined data indicative of pump vibration during inflation and/or deflation of the first and/or second selectively inflatable compartments in a similar manner.

Although the disclosed subject matter has been disclosed with reference to various particular embodiments, it is understood that equivalents may be employed and substitutions made herein without departing from the scope of the disclosed subject matter as recited in the claims.

Having described the disclosed subject matter, what is claimed as new and desired to be secured by Letter Patents is:

1. A support surface overlay system comprising:

a bladder having a first selectively inflatable compartment and a first fluid conduit in fluid communication with the first selectively inflatable compartment; and a control system configured to selectively inflate and deflate the bladder and to detect a presence of a load on the bladder, the control system comprising:

a controller having a pump configured to selectively inflate and deflate the first selectively inflatable compartment and a pump outlet conduit in fluid communication with the pump;

a memory configured to store predetermined data indicative of a first operating parameter related to inflation and deflation of the first selectively inflatable compartment with the bladder in an unloaded state as a function of time;

a first sensor configured to detect and provide data signals indicative of the first operating parameter related to inflation and deflation of the first selectively inflatable compartment as a function of time; and a processor configured to receive the data signals from the first sensor, compare the data signals received from the first sensor to the predetermined data stored in the memory according to a predetermined criteria, and determine whether or not a load is present on the bladder based on the comparison;

wherein the first operating parameter comprises sound in, on, or near one of the first fluid conduit and the pump outlet conduit as a function of time;

wherein the predetermined data stored in the memory is indicative of an unloaded-state profile of the sound in, on, or near the one of the first fluid conduit and the pump outlet conduit as a function of time; and wherein the first sensor comprises a first acoustic sensor physically associated with the one of the first fluid conduit and the pump outlet conduit by being disposed within the one of the first fluid conduit and the pump outlet conduit, attached to an exterior surface of the one of the first fluid conduit and the pump outlet conduit, or separated therefrom while configured to detect the sound in, on, or near the one of the first fluid conduit and the pump outlet conduit.

2. The support surface overlay system of claim 1, wherein the predetermined data stored in the memory comprises at least one of a duration, a timing, or a pitch characteristic; and wherein the predetermined criteria comprises a predetermined difference between at least one of the duration, the timing, or the pitch characteristic of the predetermined data stored in the memory and a corresponding one of a duration, a timing, or a pitch characteristic of the sound detected by the first sensor.

3. The support surface overlay system of claim 1, wherein the support surface overlay system further includes an exhaust conduit in fluid communication with the first selectively inflatable compartment and configured to discharge fluid from the first selectively inflatable compartment;

wherein the first operating parameter comprises sound in, on, or near the exhaust conduit as a function of time;

wherein the predetermined data stored in the memory is indicative of the sound in, on, or near the exhaust conduit as a function of time; and wherein the first sensor comprises a first acoustic sensor configured to detect the sound in, on, or near the exhaust conduit as a function of time.

4. The support surface overlay system of claim 3, wherein the predetermined data stored in the memory comprises at least one of a duration, a timing, or a pitch characteristic; and wherein the predetermined criteria comprises a predetermined difference between at least one of the duration, the timing, or the pitch characteristic of the predetermined data stored in the memory and a corresponding one of a duration, a timing, or a pitch characteristic of the sound detected by at least one of the first sensor and a second sensor.

5. The support surface overlay system of claim 3, wherein the load may comprise a patient.

6. The support surface overlay system of claim 1, wherein the bladder further comprising:

a second selectively inflatable compartment and a second fluid conduit in fluid communication with the second selectively inflatable compartment, wherein the pump is configured to selectively inflate and deflate the second selectively inflatable compartment;

a second sensor configured to detect and provide data signals indicative of a second operating parameter related to inflation and deflation the second selectively inflatable compartment as function of time, wherein the processor is further configured to receive data signals from the second sensor, compare the data signals received from the second sensor to the predetermined data stored in the memory according to the predetermined criteria, and determine whether or not a load is present on the bladder based on the comparison.

7. The support surface overlay system of claim 1, wherein the first sensor comprises one of a microphone and an accelerometer.

* * * * *